(12) United States Patent
Berthiaume et al.

(10) Patent No.: US 8,721,587 B2
(45) Date of Patent: May 13, 2014

(54) DELIVERY SYSTEM ASSEMBLIES AND ASSOCIATED METHODS FOR IMPLANTABLE MEDICAL DEVICES

(75) Inventors: William A. Berthiaume, Santa Rosa, CA (US); H. Allan Steingisser, Windsor, CA (US); Don H. Tran, Novato, CA (US); Erik Griswold, Penngrove, CA (US); Brent L. Locsin, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 119 days.

(21) Appl. No.: 13/298,973

(22) Filed: Nov. 17, 2011

(65) Prior Publication Data

US 2013/0131591 A1    May 23, 2013

(51) Int. Cl.
  *A61M 25/01*  (2006.01)
  *A61M 31/00*  (2006.01)
  *A61M 5/142*  (2006.01)
  *A61K 9/00*  (2006.01)

(52) U.S. Cl.
  CPC ........... *A61M 25/0147* (2013.01); *A61M 31/00* (2013.01); *A61M 5/14276* (2013.01); *A61K 9/0024* (2013.01)
  USPC ...................... 604/95.04; 604/528; 604/891.1

(58) Field of Classification Search
  CPC ............ A61M 31/00; A61M 25/0147; A61M 5/14276
  USPC ........ 128/899; 600/12; 604/95.04, 528, 891.1
  See application file for complete search history.

(56) References Cited

U.S. PATENT DOCUMENTS

| | | |
|---|---|---|
| 4,676,249 A | 6/1987 | Arenas et al. |
| 5,040,543 A | 8/1991 | Badera et al. |
| 5,147,379 A | 9/1992 | Sabbaghian et al. |
| 6,408,214 B1 | 6/2002 | Williams et al. |
| 7,967,798 B2 | 6/2011 | Reydel et al. |
| 2004/0116994 A1* | 6/2004 | De Bellis ...................... 607/123 |
| 2006/0004305 A1 | 1/2006 | George et al. |
| 2008/0021532 A1* | 1/2008 | Kveen et al. .................. 607/115 |
| 2009/0005846 A1* | 1/2009 | Zhu et al. ...................... 607/126 |
| 2010/0030294 A1* | 2/2010 | Wong et al. ..................... 607/30 |
| 2010/0204766 A1* | 8/2010 | Zdeblick et al. .............. 607/119 |
| 2011/0144572 A1 | 6/2011 | Kassab et al. |

(Continued)

OTHER PUBLICATIONS (PCT/US2012/065264) PCT Notification of Transmittal of the International Search Report and the Written Opinion of the International Searching Authority.

*Primary Examiner* — Jason Flick
*Assistant Examiner* — Gerald Landry, II
(74) *Attorney, Agent, or Firm* — Reed A. Duthler

(57) ABSTRACT

A delivery system assembly includes an elongate outer tube, an elongate inner member extending within a lumen of the outer tube, and an articulation sheath surrounding the outer tube between a handle of the assembly and a distal-most portion of the outer tube. The outer tube is longitudinally moveable within the sheath; and an inner diameter of the sheath is preferably smaller than that of the handle and the distal-most portion of the outer tube. Navigation of the assembly through a venous system, for deployment of an implantable medical device, is facilitated by deflection of the sheath, to orient a distal-most portion of the outer tube, within which an entirety of the medical device is contained/loaded, and by subsequent advancement of the distal-most portion, with respect to the sheath, to move the distal end of the inner member, along with the contained/loaded device into proximity with a target implant site.

17 Claims, 7 Drawing Sheets

(56) References Cited

U.S. PATENT DOCUMENTS

| | | | |
|---|---|---|---|
| 2012/0053651 A1* | 3/2012 | Zhu et al. | 607/23 |
| 2012/0172892 A1* | 7/2012 | Grubac et al. | 606/129 |
| 2012/0245679 A1* | 9/2012 | Solem | 623/3.11 |
| 2013/0103047 A1* | 4/2013 | Steingisser et al. | 606/129 |
| 2013/0131693 A1* | 5/2013 | Berthiaume et al. | 606/129 |

* cited by examiner

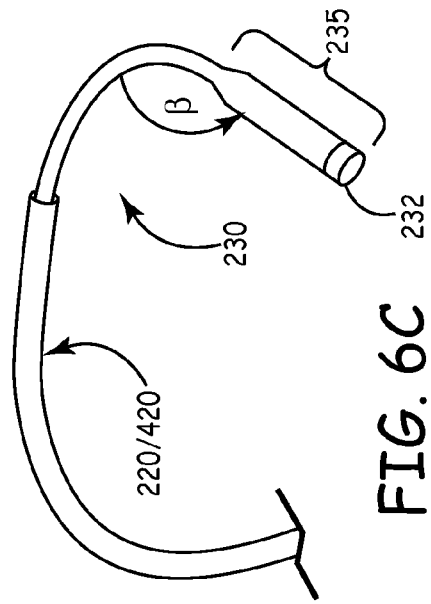
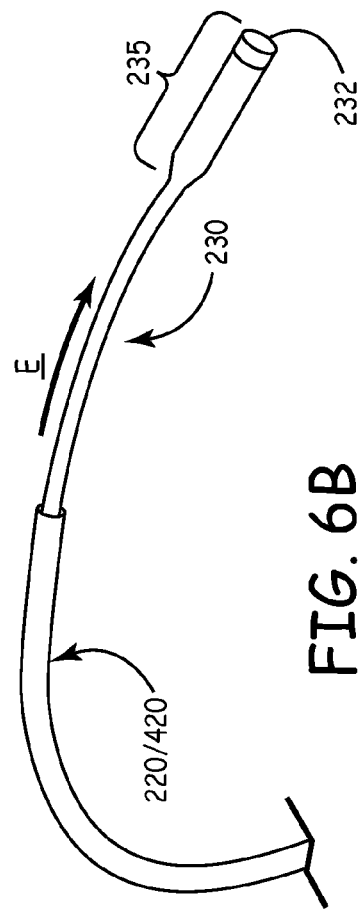
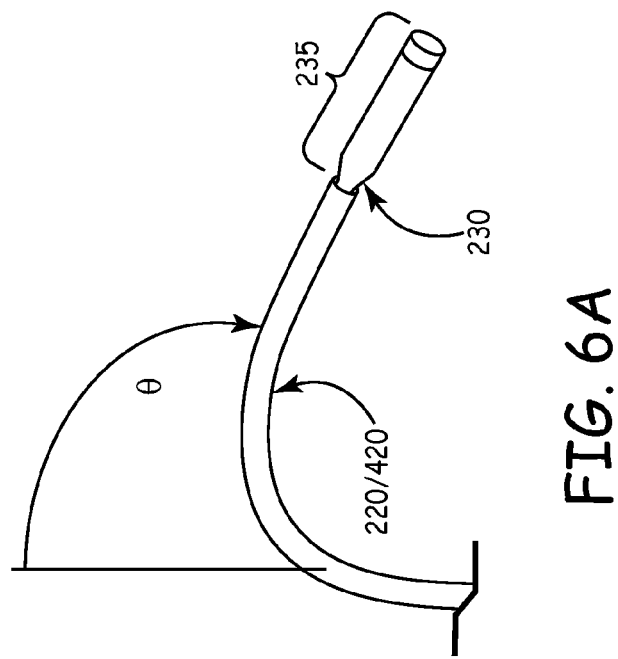
FIG. 6A
FIG. 6B
FIG. 6C

DELIVERY SYSTEM ASSEMBLIES AND ASSOCIATED METHODS FOR IMPLANTABLE MEDICAL DEVICES

CROSS-REFERENCE TO RELATED APPLICATIONS

The present application is related to the following co-pending and commonly-assigned U.S. patent applications: application Ser. No. 13/298,821 entitled DELIVERY SYSTEM ASSEMBLIES FOR IMPLANTABLE MEDICAL DEVICES and filed on even date herewith; application Ser. No. 13/239,990 entitled DELIVERY SYSTEM ASSEMBLIES FOR IMPLANTABLE MEDICAL DEVICES, and filed on Sep. 22, 2011; application Ser. No. 13/279,835 entitled DELIVERY SYSTEM ASSEMBLIES AND ASSOCIATED METHODS FOR IMPLANTABLE MEDICAL DEVICES, and filed on Oct. 24, 2011; and application Ser. No. 13/219,279 entitled HOLDING MEMBERS FOR IMPLANTABLE CARDIAC STIMULATION DEVICES, and filed on Aug. 26, 2011.

FIELD OF THE DISCLOSURE

The present invention pertains to the delivery of implantable medical devices, and more particularly to system assemblies and associated methods that facilitate percutaneous transvenous deployment of relatively compact implantable cardiac medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of cardiac pacing devices that are wholly contained within a relatively compact package for implant in close proximity to the pacing site, for example, within the right ventricle (RV) of the heart. With reference to FIG. 1, such a device 100 is illustrated, wherein pace/sense electrodes 111, 112 are formed on an exterior surface of an enclosure that hermetically contains a pulse generator including pulse generator electronics and a power source. FIG. 1 illustrates a fixation member 115 mounted to an end of the enclosure of device 100, in proximity to electrode 111, in order to fix, or secure electrode 111 against the endocardial surface in the apex of the RV. The enclosure may be formed from a biocompatible and biostable metal such as titanium overlaid with an insulative layer, for example, medical grade polyurethane or silicone, except where electrode 112 is formed as an exposed portion of capsule 101. A hermetic feedthrough assembly (not shown), such as any known to those skilled in the art, may couple electrode 111 to the pulse generator that is contained within the enclosure of device 100.

FIG. 1 further illustrates a distal portion of a standard guiding catheter 150 having been maneuvered up through the inferior vena cava (IVC) and into the RV from the right atrium (RA), according to methods known in the art of interventional cardiology. Although catheter 150 may be employed to deliver device 100 to the RV, for implant, more sophisticated delivery systems that facilitate improved navigation and deployment more suitable for relatively compact implantable devices, like device 100, are desired.

SUMMARY

A delivery system assembly, according to some embodiments of the present invention, includes an elongate outer tube, an elongate inner member, which extends within a lumen formed by the outer tube, and an articulation sheath that surrounds the outer tube. The outer tube is moveable within the articulation sheath, so that the outer tube may be longitudinally moved, proximally and distally, relative to the articulation sheath. According to some preferred embodiments, the sheath has an inner diameter that is smaller than an outer diameter of a distal-most portion of the outer tube, and smaller than an outer diameter of a handle of the delivery system assembly from which the outer tube extends.

Navigation of the delivery system assembly through a venous system of a patient, according to some methods of the present invention, is facilitated by deflection of the articulation sheath, to orient the distal-most portion of the outer tube, and by subsequent advancement/extension of the outer tube with respect to the articulation sheath to move the distal-most portion into proximity with a target implant site. According to some embodiments, the articulation sheath includes a pull-wire member for deflection of a distal end of the sheath to orient the distal-most portion of the outer tube. According to some alternate embodiments, a distal segment of the articulation sheath has a pre-formed curvature, wherein the curvature is initially straightened with a straightening mandrel that is fully inserted within a lumen of the inner member, and then released for deflection of the sheath to orient the distal-most portion of the outer tube. The lumen formed by the outer tube, along a length of a distal-most portion of the outer tube, is sized to contain an entirety of an implantable medical device; and a distal end of the inner member is preferably configured to conform to a proximal end of the medical device and to engage within the distal-most portion at a location that allows the engaged distal end and the entirety of the medical device to be contained, together, within the distal-most portion of the outer tube. When the distal end of the inner member is engaged within the distal-most portion of the outer tube, the advancement/extension of the outer tube, from the proximal position toward the distal position, causes similar longitudinal movement of the inner member. When the outer tube is retracted, or moved proximally, for example, via a control member of the handle of the assembly, the distal end of the inner member is disengaged from the distal-most portion so that the outer tube moves independently of the inner member, relative to both the articulation sheath and the inner member.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements.

FIGS. 6A-C are schematics showing portions of the delivery system assemblies in various states for navigation, according to some embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
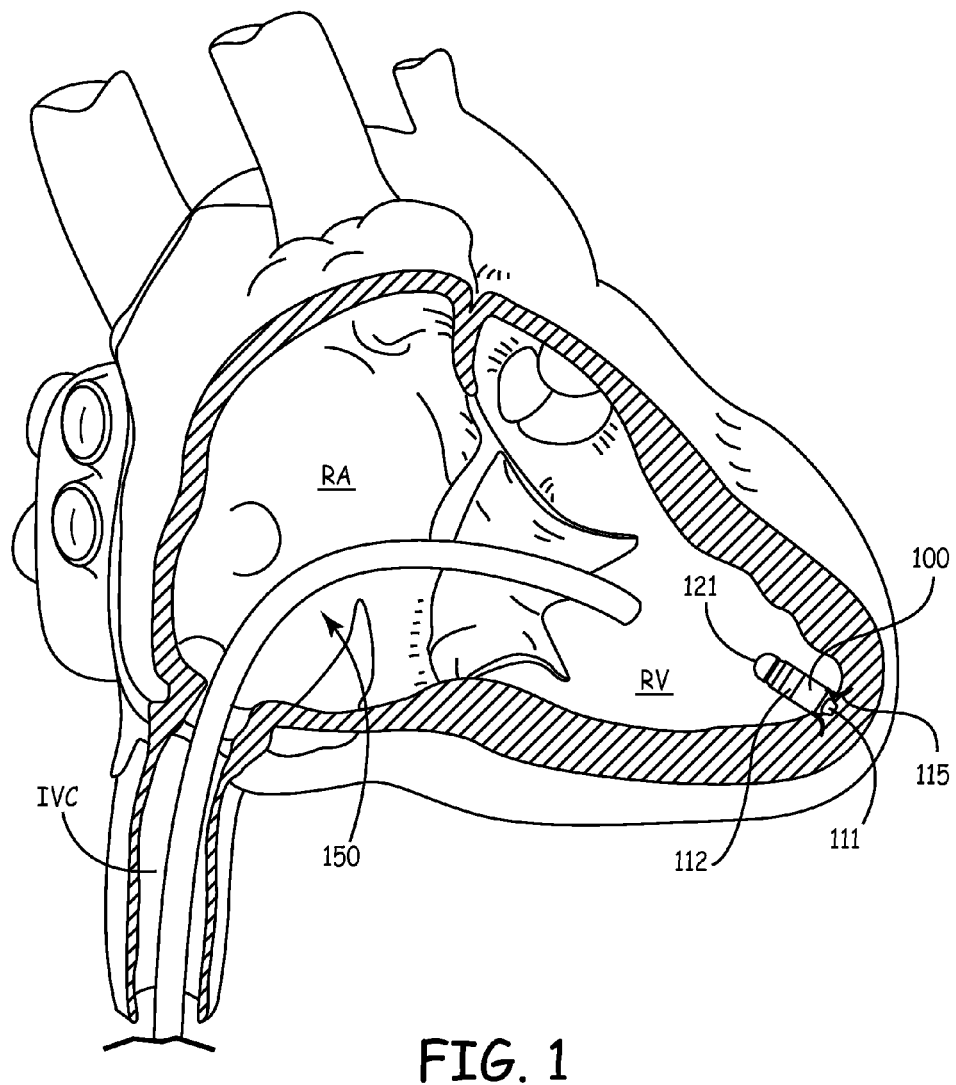
FIG. 1 is a schematic showing an example of an implanted cardiac stimulation device.
Figure 2A:
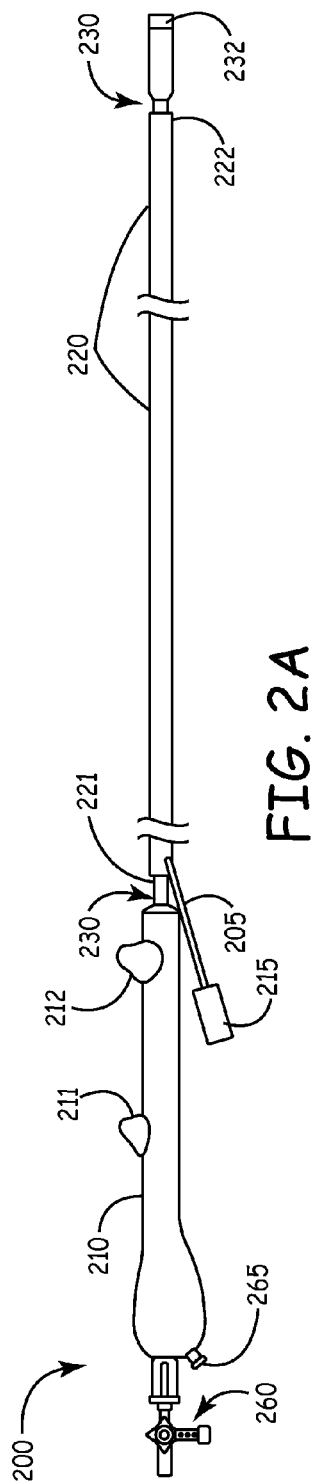
FIG. 2A is a plan view of a delivery system assembly, according to some embodiments.
Figure 2B:
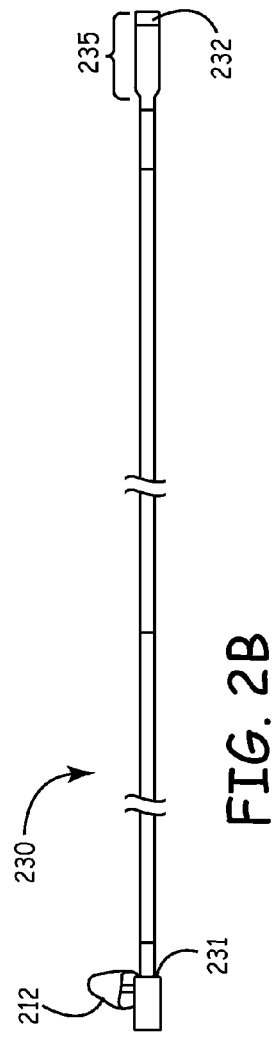
FIGS. 2B-C are plan views of outer and inner subassemblies, respectively, of the system assembly shown in FIG. 2A, according to some embodiments.
Figure 2C:
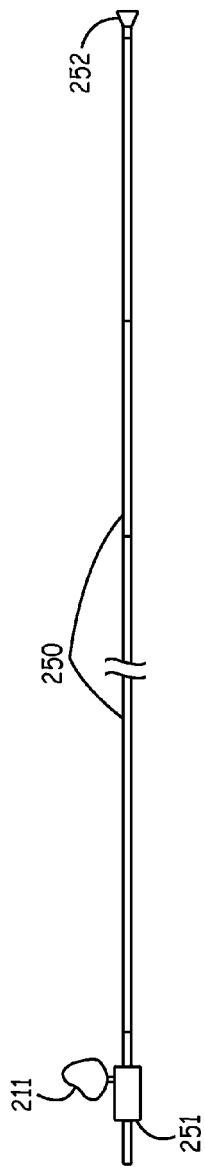

FIG. 2A is a plan view of a delivery system assembly 200, according to some embodiments; and FIGS. 2B-C are plan views of outer and inner subassemblies, respectively, of assembly 200, according to some embodiments. FIG. 2A illustrates system assembly including a handle 210 having a control member 212 and from which an elongate outer tube 230 extends in a distal direction; and FIG. 2B illustrates a proximal end 231 of outer tube 230 inserted within a ring of control member 212 and bonded thereto, for example, by a UV cure adhesive. According to the illustrated embodiment, outer tube 230 forms a lumen 236 (FIGS. 3 and 5) within which an elongate inner member 250 (FIG. 2C) extends. FIG. 2B further illustrates outer tube 230 extending from proximal end 231 to a distal-most portion 235 that is terminated by a distal end 232 of outer tube 230; and, it should be understood that, lumen 236 formed by outer tube 230 preferably has a proximal opening at proximal end 231 and a distal opening at distal end 232. With further reference to FIG. 2A, assembly 200 further includes an articulation sheath 220, which surrounds outer tube 230 in between handle 210 and distal-most portion 235. According to embodiments of the present invention, outer tube 230 is longitudinally moveable within articulation sheath 220, and articulation sheath 220 preferably has an inner surface 228 spaced apart from outer tube 230 by a radial gap, for example, being between approximately 0.002 inch and approximately 0.01 inch. FIGS. 2A-B further illustrate distal-most portion 235 being enlarged from a remainder of outer tube 230, preferably having an outer diameter that is approximately equal to an outer diameter of articulation sheath 220 and greater than an inner diameter of sheath 220, for example, the outer diameter of distal-most portion 235 being approximately 0.30 inch (~0.8 cm), over a length of approximately 3.5 cm (~1.4 inch), and the inner diameter of sheath 220 being approximately 0.275 inch (~0.7 cm). A maximum distance between handle 210 and distal-most portion 235 of outer tube, for example, when outer tube 230 is not retracted (retraction of outer tube 230 described below), is preferably at least approximately 10 cm to 11 cm greater than a length of articulation sheath 220, for example, between approximately 95 cm and approximately 110 cm, when a length of articulation sheath 220 is between approximately 85 cm and approximately 95 cm. These lengths are suitable for navigating distal-most portion 235 of outer tube into a patient's right atrium (RA) and right ventricle (RV) from a femoral access site, for example, as described below in conjunction with FIG. 7.

Figure 3:
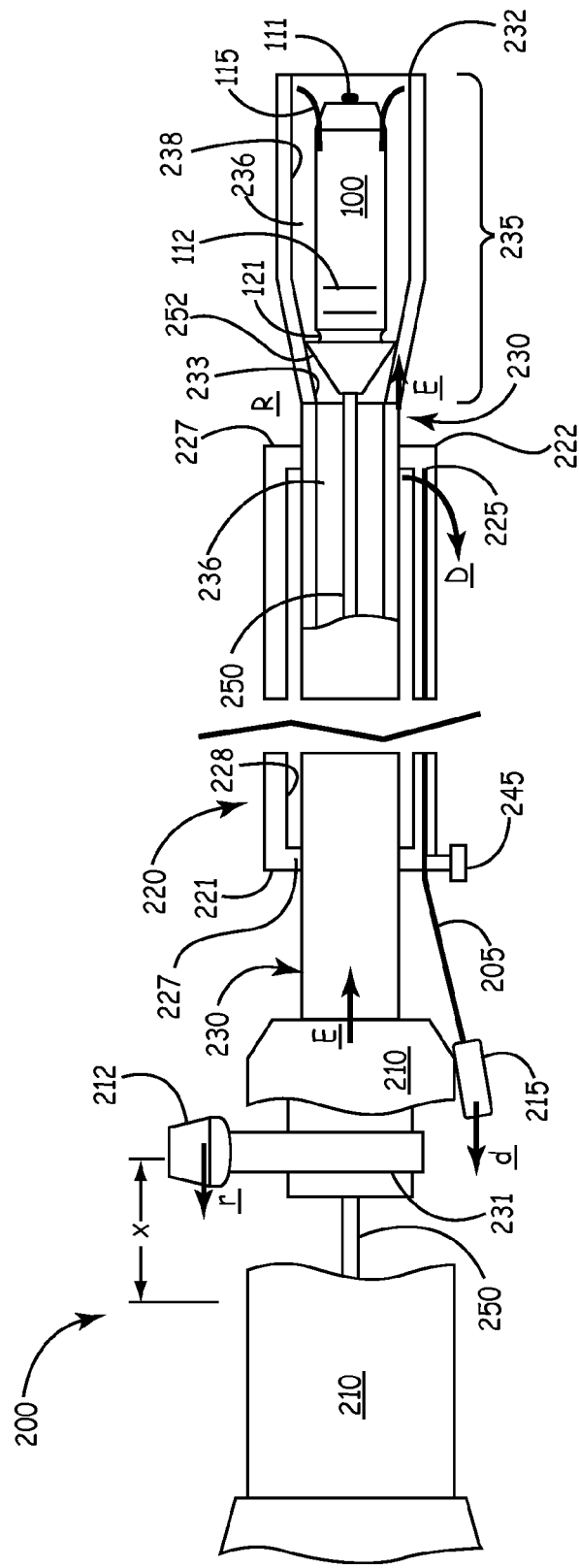
FIG. 3 is another plan view of the delivery system assembly, including detailed cut-away sections, according to some embodiments.

FIG. 2A further illustrates articulation sheath 220 including a pull-wire member 205 extending proximally from proximal end 221 of sheath 220 and being terminated by a proximal control end 215. With reference to FIG. 3, which is a plan view of assembly 200 including cut-away sections, pull-wire member 205 extends between a proximal end 221 of sheath 220 and a distal end 222 of sheath 220, and includes a distal end 225 which is anchored in proximity to distal end 222. According to the illustrated embodiment, when proximal control end 215 is pulled, per arrow d, pull-wire member 205 deflects distal end 222 of sheath 220, per arrow D. FIG. 3 further illustrates an optional locking member 245 mounted to proximal end 221 of shaft 220, for example, a screw-type fastener, which may be secured against pull-wire member 205 to hold the pulled tension therein, so as to maintain the deflection of sheath 220. According to some preferred embodiments, the shaft of sheath 220 includes a 304 medical grade stainless steel braid sandwiched between a relatively thin inner polymer liner, for example, formed from a polyether block amide, such as PEBAX® 6333, or from a high density polyethylene (HDPE), and a polymer outer jacket, preferably divided into a proximal segment and a distal segment, the distal segment of the outer jacket having a lower durometer than the proximal segment and extending over a length of approximately 3 cm. According to an exemplary embodiment, the proximal segment of the outer jacket of sheath 220 is formed from PEBAX® 7233 and the distal segment from PEBAX® 3533. Pull-wire member 205 may extend within a lumen formed within the wall of articulation sheath 220, for example, by a fluoropolymer tubing that extends between the inner liner and the outer jacket of sheath 220; and the anchored distal end 225 of pull-wire member 205 may be formed in a ring that extends about a perimeter of distal end 222 and is sandwiched, like the above-described braid between an inner layer and outer layer of the shaft of sheath 220.

Proximal and distal ends 221, 222 of articulation sheath 220 may be formed into, or may include, as illustrated in FIG. 3, relatively lubricious stabilization members 227 that form an interface with outer tube 230 to facilitate smooth longitudinal movement of outer tube 230 within sheath 220, either in conjunction with handle 210 or relative thereto, as will be described in greater detail below. Proximal end 221 of articulation sheath 220 is preferably initially located at a distance of approximately 10 cm distal to handle 210, such that handle 210 and outer tube 230 may be advanced together, per arrow E (FIG. 3), relative to sheath 220, for example, after the above-described deflection of distal end 222 of sheath 220, over a sufficient distance to place distal end 232 of outer tube into close proximity with a target implant site, as will be described below, in conjunction with FIGS. 6A-C. Distal end 222 may be initially located approximately within 1 cm of distal-most portion 235 of outer tube 230.

FIGS. 2C and 3 further illustrate elongate inner member 250 extending from a proximal end 251 thereof to an enlarged distal end 252 thereof. Although not shown, proximal end 251 may extend proximally from handle 210, through a clamping mechanism 260 (FIG. 2A), which is, for example, coupled to handle 210 by a luer fitting (not shown). FIG. 3 illustrates distal end 252 of inner member 250 engaged within distal-most portion 235 of outer tube 230 by a confronting, or abutting interface with an internal shoulder 233, so that when outer tube 230 is moved per arrow E, distal-most portion 235 and inner member 250 are moved together, in a distal direction, with respect to articulation sheath 220. With further reference to FIG. 3, when control member 212 is moved per arrow r, outer tube 230 is retracted, or moved longitudinally in a proximal direction, per arrow R, independently of inner member 250 and relative to both sheath 220 and inner member 250, since distal end 252 of inner member 250 becomes disengaged from distal-most portion 235. Thus, the retraction of outer tube 230 exposes fixation member 115 of device 100 for the deployment thereof. According to some alternate embodiments, proximal end 252 of inner member 250, which may extend proximally out from handle 210, is employed to move inner member 250 relative to outer tube 230. (It should be noted that alternate embodiments may employ other means, of similar engagement and disengagement between distal end 252 of inner member 250 and distal-most portion 235, which allow for the above-described coordinated distal movement of outer tube 230 and inner member 250 and the independent proximal movement of outer tube 230 relative to inner member 250.) In order to facilitate the movement of outer tube 230 relative to inner member 250, a biocompatible lubricant, such as MED 361 silicone oil, may be applied between outer tube 230 and inner member 250, along lengths thereof and/or between the outer surface of enlarged distal end 252 of inner member 250 and an inner surface 238 of distal-most portion 235 of outer tube 230. According to some embodiments, an O-ring type seal member (i.e. silicone; not shown), which may be lubricated, for example, with silicone oil, forms a dynamic sealing interface between outer tube 230 and inner member 250 within handle 210. The construction of articulation sheath 220 may allow an operator to grip thereabout to retract outer tube 230 without impeding the movement of outer tube 230, for example, like the stability sheath (250) that is described in the above-referenced related U.S. patent application Ser. No. 13/239,990.

With further reference to FIG. 3, an entirety of implantable medical device 100 is shown contained within distal-most portion 235 of outer tube 230, for example, having been loaded therein through a distal opening in lumen 236 of outer tube 230 at distal end 232. Distal-most portion 235 of outer tube 230 may have an inner diameter of approximately 0.275 inch (~0.7 cm). FIG. 3 further illustrates a proximal end 121 of device 100 abutting distal end 222 of inner member 220, which, is preferably configured to conform to proximal end 121. Such a conforming configuration of distal end 252 may help to retain device 100 within distal-most portion 235 of outer tube 230 during navigation of delivery system assembly 200 and prior to deployment of device 100 therefrom. According to an exemplary embodiment, enlarged distal end 252 is formed from a polyether block amide, for example, PEBAX® 7033, with a radiopaque Barium sulfate filler, and distal-most portion 235 is also formed from a polyether block amide, for example, PEBAX® 7233, which, at distal end 232, includes a radiopaque band of 75% Tungsten and 25% PEBAX® 6033 sandwiched between layers of the PEBAX® 7233. According to the illustrated embodiment, and as will be described in greater detail below, in conjunction with FIGS. 6A-C, when pull-wire member 205 of articulation sheath 220 is actuated, per arrow d, to deflect distal end 222, per arrow D, distal-most portion 235 is oriented, to facilitate navigation of assembly 200 for the deployment of device 100.

Figure 4A:
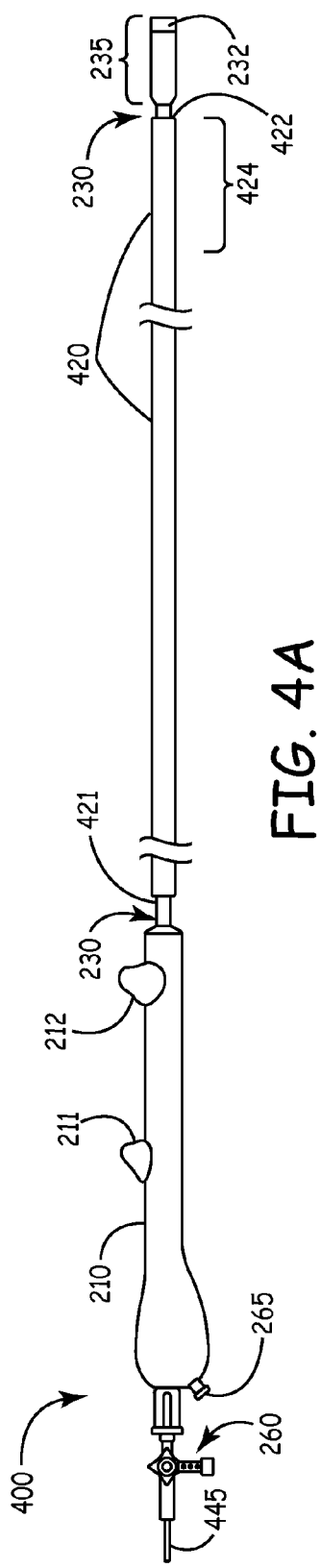
FIG. 4A is a plan view of another delivery system assembly, according to some alternate embodiments.
Figure 4B:
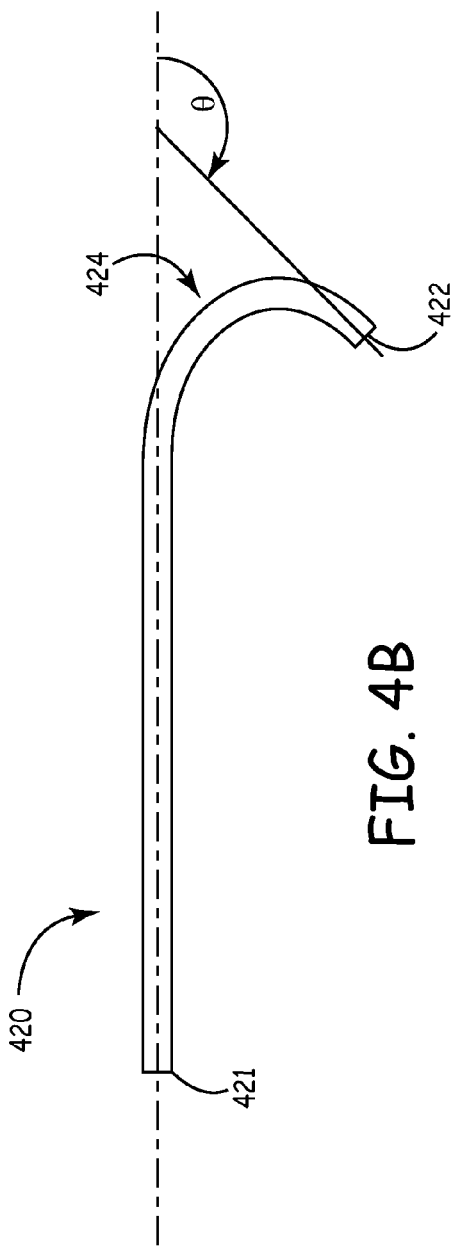
FIG. 4B is a plan view of an articulation sheath of the system assembly of FIG. 4A, in a pre-formed state, according to some embodiments.

FIG. 4A is a plan view of another delivery system assembly 400, according to some alternate embodiments; and FIG. 4B is a plan view of an articulation sheath 420 of system assembly 400, in a pre-formed state, according to some embodiments. FIG. 4A illustrates delivery system assembly 400 including outer tube 230, which, like system assembly 200, extends distally from handle 210, through a lumen of sheath 420, and is coupled to control member 212 at a proximal end 231 thereof. Although not shown in FIG. 4A, system assembly 400 further includes an inner member 450 that is similar to inner member 250 and will be described in conjunction with FIG. 5. FIG. 4A further illustrates articulation sheath 420 surrounding outer tube 230 between handle 210 and distal-most portion 235 of outer tube 230, wherein a proximal end 421 of sheath 420 is initially spaced distally from handle 210 by approximately 10 cm, when a distal end 422 of sheath 420 is located approximately 1 cm proximal to distal-most portion 235. FIG. 4B illustrates articulation sheath 420 including a distal segment 424 having a pre-formed curvature, which is straightened in assembly 400, as illustrated in FIGS. 4A and 5, by a fully inserted straightening mandrel 445.

Figure 5:
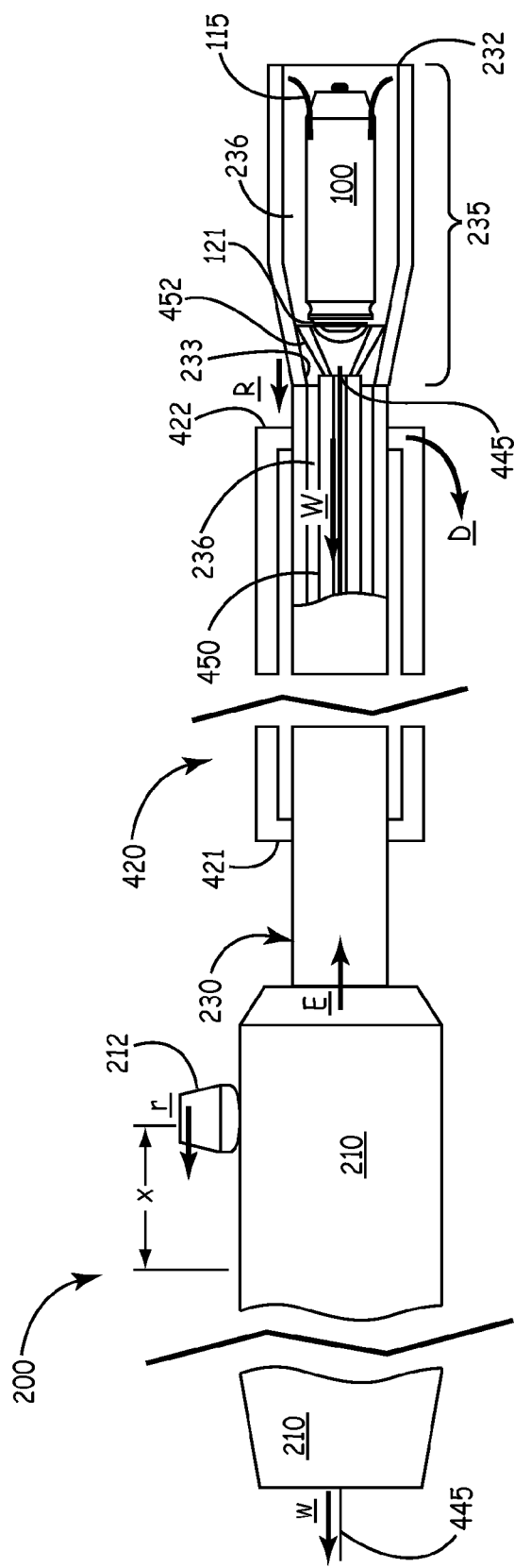
FIG. 5 is another plan view of the delivery system assembly of FIG. 4A, including detailed cut-away sections, according to some embodiments.

FIG. 5 is another plan view of the delivery system assembly 400, including detailed cut-away sections, according to some embodiments. FIG. 5 illustrates inner member 450 forming an inner lumen in which straightening mandrel 445 is fully inserted in order to straighten the pre-formed curvature of distal segment 424. Mandrel 445 is preferably formed from medical grade stainless steel and may have a diameter of between approximately 0.02 and approximately 0.04 inch (~0.5 mm and ~1 mm) and a length of between approximately 120 cm and approximately 140 cm. The fully inserted mandrel 445 is shown extending proximally, out from handle 210, and distally into proximity with a distal end 452 of inner member 450, beyond distal end 422 of sheath 420. According to the illustrated embodiment, when mandrel 445 is withdrawn, per arrow w, for example, over a distance of at least approximately 4 cm, the pre-formed curvature of distal segment 424 is released toward the configuration shown in FIG. 4B, thereby orienting distal-most portion 235, to facilitate navigation of assembly 400 for the deployment of device 100, as will be described below, in conjunction with FIGS. 6A-C and 7. With further reference to FIGS. 4A and 5, an inner surface of sheath 420, like sheath 220, is spaced apart from outer tube 230 by a radial gap, for example, being between approximately 0.002 inch and approximately 0.01 inch. Furthermore, according to some preferred embodiments, the shaft of sheath 420 is constructed similar to the above-described shaft of preferred embodiments of articulation sheath 220, and then distal segment 424 may be formed into the desired curvature, for example, by heat setting at approximately 100° C. for approximately 15 minutes; the curvature may be imparted to distal segment 424, during the heat setting, either by inserting a shaping mandrel, having the desired curvature within the lumen of sheath 420, or by constraining distal segment 424 of sheath 420 within a groove of a tray that conforms to the desired curvature.

FIG. 5 further illustrates distal end 452 of inner member 450 conforming to proximal end 121 of device 100, which is contained within distal-most portion 235 of outer tube 230. The previously described engagement of distal end 252 of inner member 250, in relation to assembly 200, may also apply to distal end 452 of inner member 450 of assembly 400, so that longitudinal movement of outer tube 230, in the distal direction, relative to sheath 420, similarly moves inner member 450; and, when outer tube 230 is moved in the opposite, proximal direction, per arrow R, distal end 452 is disengaged so that this retraction of outer tube 230 is independent of inner member 450. Likewise, in order to facilitate the movement outer tube 230 relative to inner member 450, the above-described biocompatible lubricant and O-ring type seal member may be employed in system assembly 400, at the interfaces between inner member 450 and outer tube 230, in a similar fashion to that described above for inner member 250 and outer tube 230 in system assembly 200.

FIGS. 6A-C are schematics showing portions of delivery system assemblies 200/400 in various states for navigation, according to some embodiments. FIG. 6A illustrates articulation sheath 220/420 having been deflected over angle θ, either by pull-wire member 205 (FIGS. 2A and 3) or by releasing the pre-formed curvature of distal segment 424 (FIG. 4B), to orient distal-most portion 235 of outer tube 230 for navigation in a patient's venous system, as will be described in greater detail below. An angle θ of the deflection (from the vertical line of FIG. 4A) may range from approximately 100 degrees to approximately 200 degrees. FIG. 6B illustrates outer tube 230 having been moved, in a distal direction, relative to articulation sheath 220/240, per arrow E, from the proximal position of FIG. 6A to a distal position, such that delivery system assembly 200/400 is extended, relative to sheath 220/420, to reach to a target implant site for deployment of device 100, which is contained within distal-most portion 235 of outer tube 230 (FIGS. 3 and 5). The extension of outer tube 230 relative to distal end 222/422 of sheath 220/420 may range from approximately 5 cm and approximately 10 cm. As previously described, handle 210 may be used to push outer tube 230, along with inner member 250/450, in a distal direction relative to sheath 220/420, per arrow E, wherein the aforementioned distance (i.e. ~10 cm) between proximal end 221/421 of sheath 220/420 and handle 210 allows for this advancement of outer tube 230, while sheath 220/420 is held in place. Furthermore, while outer tube 230 is advanced, the deflection of sheath 220 is preferably maintained by holding tension in pull-wire member 205, for example, either manually or via optional locking member 245 (FIG. 3).

FIG. 6C illustrates an additional deflection, per angle β, to further orient distal-most portion 235 of outer tube 230, either during or after the movement per arrow E of FIG. 6B; the additional deflection may be accomplished, according to some embodiments, by actuating a pull-wire member included in inner member 250/450. The above-referenced related U.S. patent application Ser. No. 13/239,990 describes a deflectable inner member (220), including a pull wire (225), that is suitable for incorporation within either of system assemblies 200/400, the description of which is hereby incorporated by reference; and a control member 211 of handle 210 (FIGS. 2A and 4A) may be coupled to the pull wire for actuation thereof. Once distal end 232 of outer tube 230 is positioned at the target implant site, retraction of outer tube 230, for example, via proximal movement of control member 212, exposes fixation member 115 of device 100 to engage tissue at the site, for example as alluded to above; the deployment of device 100, upon retraction of outer tube 230, is described in greater detail in the above-referenced related U.S. patent application Ser. No. 13/279,835, the description of which is hereby incorporated by reference. With reference to FIGS. 3 and 5, a maximum travel x of control member 212, along handle, moves outer tube 230 in the proximal direction, per arrow R, over a distance of approximately 10 cm.

Figure 7:
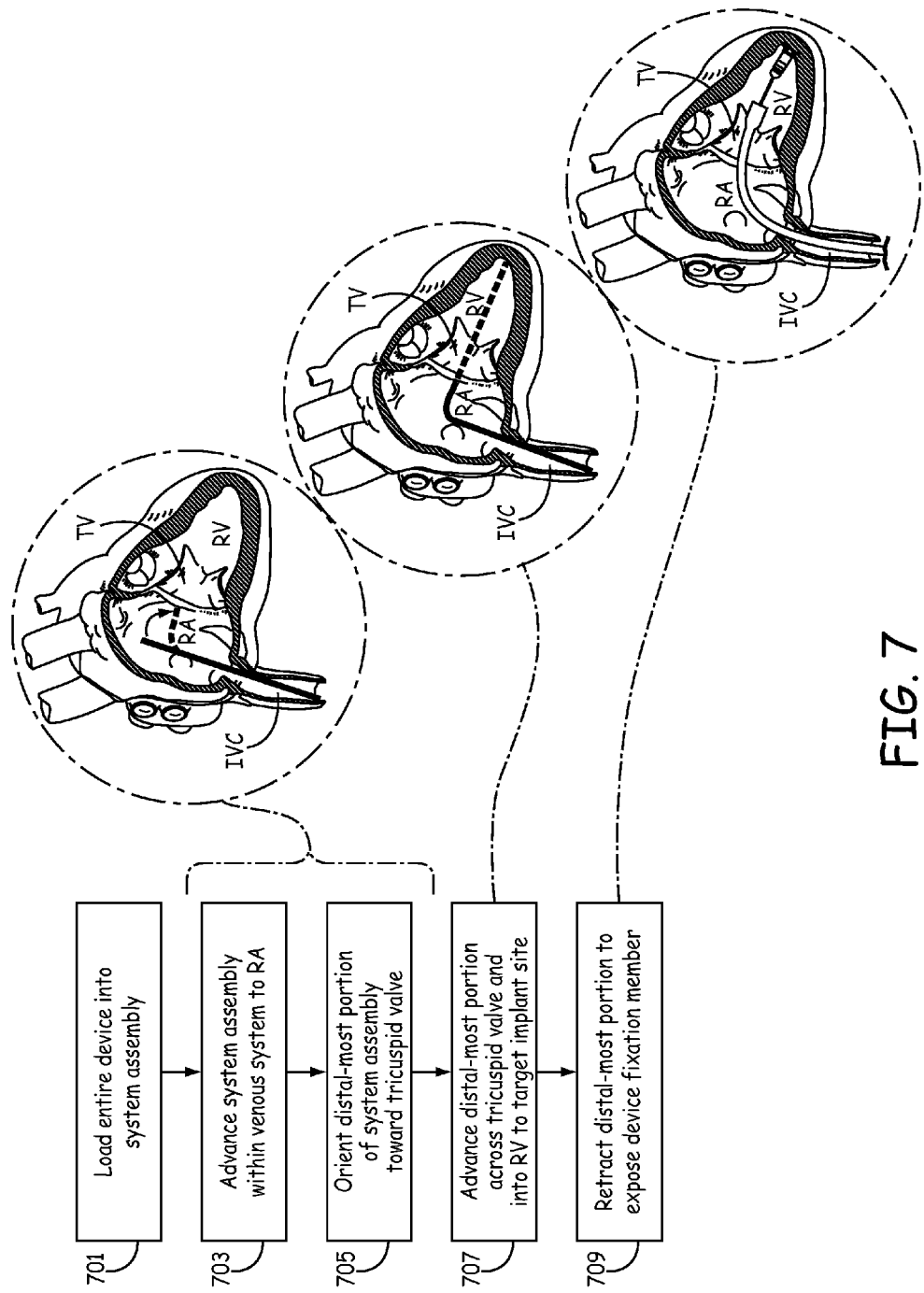
FIG. 7 is a flow chart, including some schematics, that outlines some methods of the present invention.

FIG. 7 is a is a flow chart, including some schematics, that outlines some methods of the present invention for navigating system assemblies 200/400 through a venous system of a patient for deployment of implantable medical device 100. According to an initial step 701, and with reference to FIGS. 3 and 5, device 100 is loaded into distal-most portion 235 of outer tube 230 of delivery system assembly 200/400, such that an entirety of device 100 is contained within distal-most portion 235 and proximal end 121 of device 100 abuts distal end 252/452 of inner member 250/450. According to some preferred embodiments and methods, when loading device 100, per step 701, a tether, such as that described in the above-referenced related U.S. patent application Ser. No. 13/279,835, is attached to proximal end 121 of device 100. After loading device 100, air may be purged from delivery system assembly 200/400 by flushing a fluid (i.e. saline) through lumen 236 of outer tube 230, and, in system assembly 400, through the inner lumen formed by inner member 450, for example, via a port 265 in handle 210 (FIGS. 2A and 4A); then, as positive fluid pressure is held within the lumen(s), delivery system assembly 200/400 is introduced into a patient's venous system, for example, through an introducer sheath at a femoral site. Subsequently, delivery system assembly 200 may be advanced, per step 703, into the RA (right atrium) of the heart, for example, via the IVC (inferior vena cava), at which point, distal-most portion 235 of outer tube 230 is oriented toward the tricuspid valve (TV), per step 705, preferably by deflecting articulation sheath 220/420, as described above. With reference back to FIG. 6A, the angle θ of deflection may be approximately 110 degrees to orient distal-most portion 235 toward the TV. Once oriented, distal-most portion 235 of outer tube 230 is advanced across the TV, into the RV (right ventricle), and to a target implant site, per step 707, such that distal-most portion 235 abuts the site and the distal opening of lumen 236 formed by outer tube 230, at distal end 232, is within tissue, for example, trabeculae carneae, at the site. As described above, the engagement of distal end 252/452 of inner member 250/450 causes distal end 252/452 of inner member 250/450 and device 100 to be carried along with the advanced/extended distal-most portion 235, while deflected articulation shaft 220/420 is held relatively stationary, and angle θ of the deflection is maintained relatively constant, for example, in the case of system assembly 200, by employing optional locking member 245 (FIG. 3), or by securing proximal control end 215 of pull-wire member 205, for example, with a clip member. With reference back to FIG. 6C, in those embodiments that include a deflectable inner member, some methods include a step of deflecting the inner member, per angle β, to further orient distal-most portion 235 so that distal end 232 is more precisely directed toward the target implant site.

After reaching the target implant site, distal-most portion 235 is retracted, per step 709, to expose fixation member 115 of device 100 for engagement thereof with the tissue at the site. The retraction of distal-most portion 235 may be actuated by proximal movement of control member 212, which is coupled to proximal end 231 of outer tube 230, as described above. According to some preferred methods, distal-most portion 235 may be retracted over a distance of between approximately 5 cm and approximately 10 cm, for the deployment of device 100. According to alternate methods, inner member 250/450 may be advanced relative to outer tube 230 to push device 100 distally and thereby expose fixation member 115 outside of distal-most portion 235, however the retraction of distal-most portion 235, per step 709, is the preferred means to expose fixation member 115, so as to prevent injury, for example, perforation by excess push force, at the target implant site. Additional steps in the deployment of device 100, that may follow step 709, are described in the above-referenced related U.S. patent application Ser. No. 13/279,835.

The construction of shafts for inner member 250/450 and outer tube 230 may be any suitable type known in the art to achieve suitable graduated flexibility for the necessary maneuverability thereof, which includes pushability and torque transfer, as well as the above described deflection, for navigation within the venous system of a patient, as described above. According to an exemplary embodiment, the shaft of inner member 250 extends over a length of approximately 118 cm, from proximal end 251 to just proximal to enlarged distal end 252, and includes a 304 medical grade stainless steel braid sandwiched between an inner liner formed from PEBAX® 7033 and a Nylon 12 jacket, all of which is overlaid by an outer jacket, wherein the outer jacket is divided into: a proximal segment of Nylon 12, which is approximately 100 cm long (including that portion which extends within handle 210); an intermediate segment of PEBAX® 5533, which extends distally from the proximal segment over a length of approximately 11 cm; and a distal segment of PEBAX® 3533, which extends distally from the intermediate segment over a length of approximately 6.5 cm. According to those embodiments in which inner member 250 is deflectable, the outer jacket may include a lumen in which a pull wire (i.e. 0.009" diameter 304 stainless steel) extends, and a distal end of the pull wire may be anchored in close proximity to enlarged distal end 252 of inner member, for example, in a segment of the shaft of inner member 250, which may be formed from PEBAX® 7233 and extend between the aforementioned distal segment of the shaft and distal end 252, for example, spanning a length of approximately 0.5 cm. Furthermore, according to the exemplary embodiment, outer tube 230 includes a braid reinforced liner, for example, PEBAX® 6333 with a 304 medical grade stainless steel braid (i.e. 0.0018"×0.008"×45 PPI) extending from proximal end 231 to just proximal to distal-most portion 235; a proximal segment of the shaft is overlaid with PEBAX® 7033 and extends over a length of approximately 92 cm (a proximal portion of which length is always contained within handle 210); an intermediary segment of the shaft is overlaid with PEBAX® 4033 and extends distally from the proximal segment over a length of approximately 10 cm; and a distal segment of the shaft is overlaid with PEBAX® 3533 and extends distally from the intermediary segment, over a length of approximately 3 cm, to just proximal to the distal-most portion. Outer and inner diameters of outer tube 230, along the above-described segments, may be approximately 0.187 inch (~4.75 mm) and approximately 0.154 inch (~3.91 mm), respectively.

In the foregoing detailed description, the invention has been described with reference to specific embodiments. However, it may be appreciated that various modifications and changes can be made without departing from the scope of the invention as set forth in the appended claims.

The invention claimed is:

1. A delivery system assembly facilitating deployment of an implantable medical device, the assembly comprising:
   a handle including at least one control member;
   an elongate outer tube extending distally from the handle and forming a lumen that extends from a proximal opening thereof at a proximal end of the outer tube to a distal opening thereof at a distal end of the outer tube, the proximal end of the outer tube being coupled to one of the at least one control member of the handle, the outer tube being longitudinally moveable relative to the handle, via the control member, and the outer tube including a distal-most portion having a length along which the lumen is sized to contain an entirety of the medical device therein, the distal opening of the lumen allowing passage of the medical device therethrough for the deployment;
   an elongate inner member extending within the lumen of the outer tube, the inner member including a proximal end and a distal end, the distal end being configured to conform to a proximal end of the implantable medical device and to engage within the distal-most portion of the outer tube at a location that allows the engaged distal end of the inner member and the entirety of the medical device to be contained within the distal-most portion together; and
   an articulation sheath surrounding the outer tube in between the handle and the distal-most portion of the outer tube such that the outer tube is longitudinally moveable within the sheath, the sheath including a proximal end, located distal to the handle, a distal end, and a pull-wire member extending between the proximal and distal ends of the sheath, the pull-wire member including a proximal control end and a distal end, the distal end being anchored in proximity to the distal end of the sheath for deflection thereof, and the sheath having an inner diameter that is smaller than an outer diameter of the distal-most portion of the outer tube and an outer diameter of the handle;
   wherein, when the distal end of the inner member is engaged within the distal-most portion of the outer tube, longitudinal movement of the outer tube, in a distal direction, relative to the articulation sheath, causes similar longitudinal movement of the inner member; and
   when the outer tube is moved longitudinally in a proximal direction, relative to the handle, the distal end of the inner member is disengaged within the distal-most portion of the outer tube so that the movement of the outer tube is independent of the inner member.

2. The assembly of claim 1, wherein the length of the articulation sheath is between approximately 85 cm and approximately 95 cm.

3. The assembly of claim 1, wherein a maximum distance between the handle and the distal end of the outer tube is between approximately 95 cm and approximately 110 cm.

4. The assembly of claim 1, wherein, when the distal end of the articulation sheath is located within approximately 1 cm from the distal-most portion of the outer tube, the proximal end of the articulation sheath is located at a distance of approximately 10 cm distal to the handle.

5. The assembly of claim 1, wherein a maximum travel for the one of the at least one control member along the handle moves the outer tube in the proximal direction over a distance of approximately 10 cm.

6. The assembly of claim 1, wherein the articulation sheath comprises a braid structure sandwiched between an inner polymer liner and a polymer outer jacket, the polymer outer jacket being divided into a proximal segment and a distal segment, the distal segment having a lower durometer than the proximal segment and extending over a length of approximately 3 cm.

7. The assembly of claim 1, wherein the inner member further includes a pull-wire extending between the proximal and distal ends thereof, a proximal end of the pull-wire of the inner member being coupled to another of the at least one control member and a distal end of the pull-wire being anchored in close proximity to the distal end thereof.

8. The assembly of claim 1, wherein:
   the outer tube further includes an internal shoulder defining a proximal end of the distal-most portion of the outer tube; and
   the distal end of the inner member engages within the lumen of the outer tube by abutting the internal shoulder.

9. The assembly of claim 1, wherein the distal end of the inner member is radiopaque.

10. A delivery system assembly facilitating deployment of an implantable medical device, the assembly comprising:
   a handle including at least one control member;
   an elongate outer tube extending distally from the handle and forming a lumen that extends from a proximal opening thereof at a proximal end of the outer tube to a distal opening thereof at a distal end of the outer tube, the proximal end of the outer tube being coupled to one of the at least one control member of the handle, the outer tube being longitudinally moveable relative to the handle, via the control member, and the outer tube including a distal-most portion having a length along which the lumen is sized to contain an entirety of the medical device therein, the distal opening of the lumen allowing passage of the medical device therethrough for the deployment;
   an elongate inner member extending within the lumen of the outer tube and forming an inner lumen that extends from a proximal opening thereof at a proximal end of the inner member to a distal opening thereof at a distal end of the inner member, the distal end of the inner member being configured to conform to a proximal end of the implantable medical device and to engage within the distal-most portion of the outer tube at a location that allows the engaged distal end of the inner member and the entirety of the medical device to be contained within the distal-most portion together;
   an articulation sheath surrounding the outer tube in between the handle and the distal-most portion of the outer tube such that the outer tube is longitudinally moveable within the sheath, the sheath including a proximal end, located distal to the handle, and a distal segment having a pre-formed curvature, and the sheath having an inner diameter that is smaller than an outer diameter of the distal-most portion of the outer tube and an outer diameter of the handle; and
   a straightening mandrel configured to slide within the inner lumen of the inner member and having a length sufficient to straighten the pre-formed curvature of the distal segment of the articulation sheath when the mandrel is fully inserted within the inner lumen of the inner member;
   wherein, when the distal end of the inner member is engaged within the distal-most portion of the outer tube, the longitudinal movement of the outer tube, in a distal direction, relative to the articulation sheath, causes similar longitudinal movement of the inner member; and
   when the outer tube is moved longitudinally in a proximal direction, relative to the handle, the distal end of the inner member is disengaged within the distal-most portion of the outer tube so that the movement of the outer tube is independent of the inner member.

11. The assembly of claim 10, wherein the length of the articulation sheath is between approximately 85 cm and approximately 95 cm.

12. The assembly of claim 10, wherein a maximum distance between the handle and the distal end of the outer tube, when the outer tube is in the proximal position, is between approximately 95 cm and approximately 110 cm.

13. The assembly of claim 10, wherein a maximum travel for the one of the at least one control member along the handle moves the outer tube in the proximal direction over a distance of approximately 10 cm.

14. The assembly of claim 10, wherein the articulation sheath comprises a braid structure sandwiched between an inner polymer liner and a polymer outer jacket, the polymer outer jacket being divided into a proximal segment and a distal segment, the distal segment having a lower durometer than the proximal segment and extending over a length of approximately 3 cm.

15. The assembly of claim 10, wherein the inner member further includes a pull-wire extending between the proximal and distal ends thereof, a proximal end of the pull-wire of the inner member being coupled to another of the at least one control member and a distal end of the pull-wire being anchored in close proximity to the distal end thereof.

16. The assembly of claim 10, wherein:
   the outer tube further includes an internal shoulder defining a proximal end of the distal-most portion of the outer tube; and
   the distal end of the inner member engages within the lumen of the outer tube by abutting the internal shoulder.

17. The assembly of claim 10, wherein the distal end of the inner member is radiopaque.

* * * * *